United States Patent
Suh et al.

(10) Patent No.: US 6,515,116 B2
(45) Date of Patent: Feb. 4, 2003

(54) METHOD OF PREPARING FORM II CRYSTALS OF CLARITHROMYCIN

(75) Inventors: Kwee-Hyun Suh, Kyungki-do (KR); Sang-Min Yun, Kyungki-do (KR); Mi-Ra Seong, Kyungki-do (KR); Gi-Jeong Kim, Seoul (KR); Gwan-Sun Lee, Seoul (KR); Nam-Du Kim, Kyungki-do (KR)

(73) Assignee: Hanmi Pharm. Co., (KR)

( * ) Notice: Subject to any disclaimer, the term of this patent is extended or adjusted under 35 U.S.C. 154(b) by 0 days.

(21) Appl. No.: 09/805,831

(22) Filed: Mar. 14, 2001

(65) Prior Publication Data

US 2001/0039333 A1 Nov. 8, 2001

(30) Foreign Application Priority Data

Mar. 15, 2000 (KR) ............................................. 00-13033
Nov. 23, 2000 (KR) ............................................. 00-69834

(51) Int. Cl.⁷ ............................ C07H 17/08; C07H 1/00
(52) U.S. Cl. ........................ 536/7.2; 536/7.4; 536/18.5
(58) Field of Search ........................ 536/7.4, 7.2, 18.5

(56) References Cited

U.S. PATENT DOCUMENTS 6,258,785 B1 * 7/2001 Su et al. ....................... 514/29

FOREIGN PATENT DOCUMENTS

WO    WO 98/04574    5/1998

* cited by examiner

*Primary Examiner*—Elli Peselev
(74) *Attorney, Agent, or Firm*—Anderson Kill & Olick, P.C.

(57) ABSTRACT

High purity Form II crystals of clarithromycin can be easily prepared in a high yield by a process comprising the steps of: protecting the 9-oxime hydroxy group of erythromycin A 9-oxime or a salt thereof with a tropyl group and the 2'- and 4"-hydroxy groups with trimethylsilyl groups; reacting 2',4"-O-bis(trimethylsilyl)erythromycin A 9-O-tropyloxime with a methylating agent; removing the protecting groups and the oxime group of 2',4"-O-bis(trimethylsilyl)-6-O-methylerythromycin A 9-O-tropyloxime to obtain crude clarithromycin; treating the crude clarithromycin with methanesulfonic acid in a mixture of a water-miscible organic solvent and water to obtain crystalline clarithromycin mesylate trihydrate; and neutralizing the crystalline clarithromycin mesylate trihydrate with aqueous ammonia in a mixture of a water-miscible organic solvent and water.

18 Claims, 4 Drawing Sheets

METHOD OF PREPARING FORM II CRYSTALS OF CLARITHROMYCIN

FIELD OF THE INVENTION

The present invention relates to a method of preparing Form II crystals of clarithromycin; and to novel intermediates used in said method.

BACKGROUND OF THE INVENTION

Clarithromycin, 6-O-methylerythromycin A, is a semisynthetic macrolide antibiotic of formula (I) which exhibits strong antibacterial activity toward a wide range of bacteria inclusive of gram positive bacteria, some gram negative bacteria, anaerobic bacteria, Mycoplasma, Chlamidia and *Helicobacter pylori*, and in virtue of its high stability in the acidic environment of the stomach, it can be orally administered to treat many infectious diseases, and also to prevent recurrence of ulcer when used in a combination with other medicines:

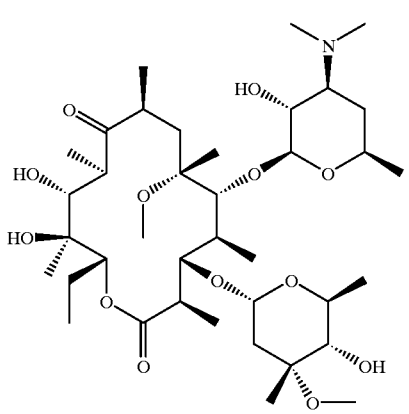

(I)

It has been reported that clarithromycin exists in at least three distinct crystalline forms, "Form 0", "Form I" and "Form II" (International Publication Nos. WO 98/04573 and WO 98/31699). The crystal forms can be identified by infrared spectroscopy, differential scanning calorimetry and powder X-ray diffraction spectrophotometry. Form II, which is thermodynamically more stable than Form I, is used in the drug formulations currently on the market.

Various methods for preparing clarithromycin have been reported, e.g., in EP Patent Nos. 0,147,062, 0,158,467, 195,960 and 260,938; and U.S. Pat. Nos. 4,990,602, 5,837, 829, 5,929,219, 5,892,008, 5,864,023 and 5,852,180. The most widely used methods use an erythromycin A 9-oxime derivative as an intermediate, which are described below.

Method 1) disclosed in EP Patent No. 0,158,467 comprises the steps of: protecting the oxime hydroxy group as well as the 2'-hydroxy group and 3'-dimethylamino group of erythromycin A 9-oxime with a benzyl group and benzyloxycarbonyl groups, respectively; methylating the 6-hydroxy group; and removing the protecting groups and the oxime group to obtain clarithromycin. However, this method requires the use of excessive amount of corrosive and toxic benzyloxycarbonyl chloride and is not amenable to commercialization due to the involvement of hydrogenolysis steps, which are difficult to use on a commercial scale.

Method 2) disclosed in EP Patent No. 0,195,960 comprises the steps of: protecting the oxime hydroxy, 2'-hydroxy and 3'-dimethylamino groups of erythromycin A 9-oxime with benzyl groups; methylating the 6-hydroxy group; and removing the protecting groups and the oxime group to obtain clarithromycin. However, this method suffers from several problems occurred in removing the protecting group.

Method 3) disclosed in EP Patent No. 0,260,938 comprises the steps of: protecting the oxime hydroxy group of erythromycin A 9-oxime with a benzyl or substituted benzyl group; protecting the 2'- and 4"-hydroxy groups with silyl groups; methylating the 6-hydroxy group; and removing the protecting groups and the oxime group to obtain clarithromycin. In this method, however, the oxime-protecting group also is removed by way of conducting a hydrogenolysis reaction, which is not suitable for mass-production.

Further, method 4) disclosed in U.S. Pat. No. 5,837,829 comprises the steps of: protecting the oxime hydroxy group and 2'- and 4"-hydroxy groups of erythromycin A 9-oxime with silyl groups; methylating the 6-hydroxy group; and removing the protecting groups and the oxime group to obtain clarithromycin. However, this method requires an extreme anhydrous condition in the methylation step due to the instability of the 9-oxime silyl group toward water, and also has the difficulty of handling hazardous of sodium hydride.

In addition, method 5) disclosed in U.S. Pat. No. 4,990,602 comprises the steps of: protecting the oxime hydroxy group of erythromycin A 9-oxime with a ketal derivative; protecting the 2'- and 4"-hydroxy groups with silyl groups; methylating the 6-hydroxy group; and removing the protecting groups and the oxime group to obtain clarithromycin. Although this method gives a relatively high yield of 45 to 50% and high selectivity of 90% in the methylation step, it requires the use of a large excess amount (2.3 to 10 equivalents) of a oxime protecting agent.

Thus, prior art methods such as methods 1) to 5) have many problems that must be solved to obtain an improved process for making clarithromycin. Moreover, the clarithromycin product obtained by the above methods is not a pharmaceutical grade clarithromycin, which must be a pure crystal Form II of clarithromycin, but non-pharmaceutical grade clarithromycin in aspect of purity and crystallinity. Accordingly, there is required a further purification step and a special crystallization step to convert non-pharmaceutical grade clarithromycin to pure Form II crystals of clarithromycin used in the current drug formulations.

There have been reported several methods of preparing Form II crystals from non-pharmaceutical grade clarithromycin. For example, Form 0 or Form I crystals of high purity are heated under a vacuum at a temperature ranging from 70 to 110□ for a prolonged period of time to prepare Form II crystals (see International Publication Nos. WO 98/04573 and WO 98/31699), but this method has the problem of low productivity.

Alternatively, Form II crystals may be obtained by recrystallizing Form I crystals from chloroform/isopropyl ether (see *Merck Index* 12th ed., pp. 395), or by recrystallizing Form I crystals from an organic solvent or a mixture of an organic solvent and water in a moderate yield (see International Publication No. WO 98/04574). In these methods, since the conversion of Form I to Form II does not accompany purity enhancement, high purity Form I crystals must be prepared in advance from crude clarithromycin, at the expense of reduced clarithromycin yield and high manufacturing cost.

Accordingly, there has continued to exist a need to develop a high yield process for preparing high purity Form II crystals of clarithromycin.

SUMMARY OF THE INVENTION

Accordingly, it is a primary object of the present invention to provide a high yield process for preparing high purity Form II crystals of clarithromycin.

It is another object of the present invention to provide novel intermediates prepared in said method.

In accordance with one aspect of the present invention, there is provided a method of preparing Form II crystals of clarithromycin (formula I) comprising the steps of:

(a) treating non-pharmaceutical grade clarithromycin with methanesulfonic acid in a mixture of a water-miscible organic solvent and water to obtain crystalline clarithromycin mesylate trihydrate of formula (II); and (b) neutralizing the crystalline clarithromycin mesylate trihydrate obtained in step (a) with aqueous ammonia in a mixture of a water-miscible organic solvent and water; wherein non-pharmaceutical grade clarithromycin refers to clarithromycin of any purity or of any stage of crystalline including a crude product obtained from a manufacturing process thereof:

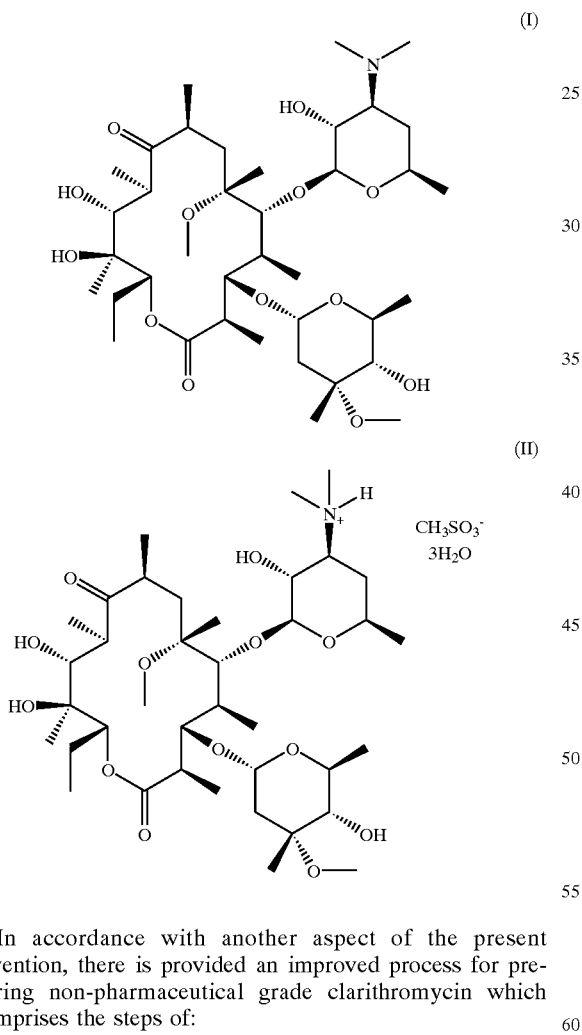

In accordance with another aspect of the present invention, there is provided an improved process for preparing non-pharmaceutical grade clarithromycin which comprises the steps of:

protecting the 9-oxime hydroxy group of erythromycin A 9-oxime of formula (IV) or a salt thereof with a tropyl group and 2'- and 4"-hydroxy groups with trimethylsilyl groups to obtain 2',4"-O-bis(trimethylsilyl) erythromycin A 9-O-tropyloxime of formula (IIIb);

reacting 2',4"-O-bis(trimethylsilyl)erythromycin A 9-O-tropyloxime with a methylating agent to obtain 2',4"-O-bis(trimethylsilyl)-6-O-methylerythromycin A 9-O-tropyloxime of formula (IIIc); and removing the protecting groups and the oxime group of 2',4"-O-bis(trimethylsilyl)-6-O-methylerythromycin A 9-O-tropyloxime:

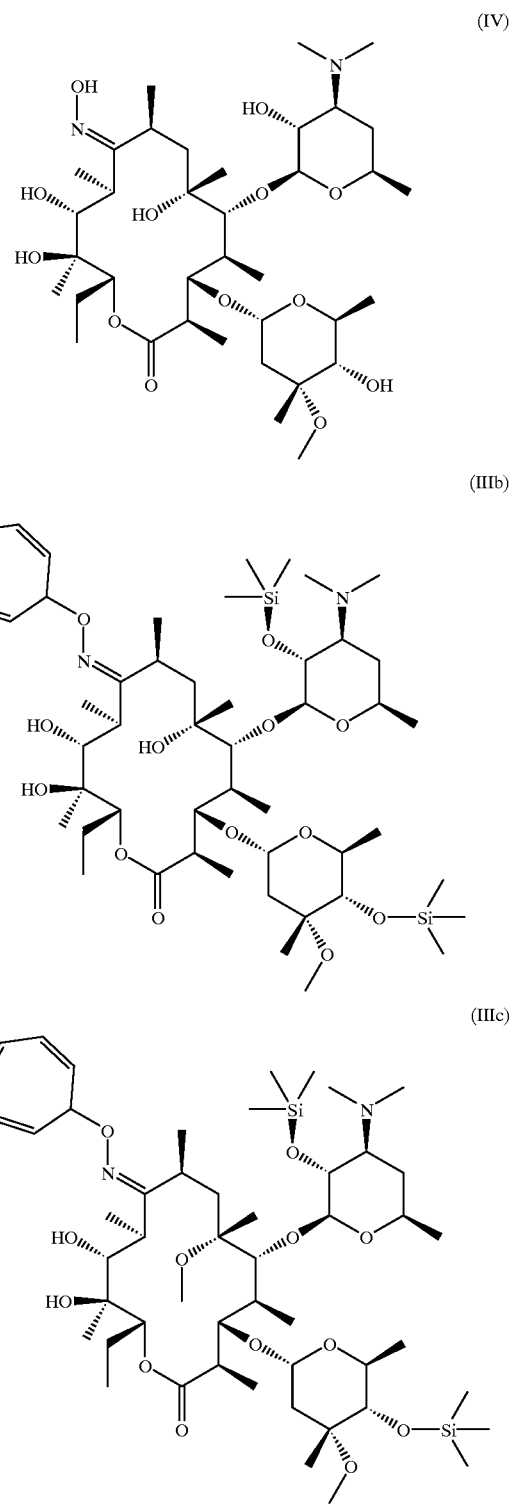

In accordance with still another aspect of the present invention, there are provided crystalline clarithromycin mesylate trihydrate of formula (II); and erythromycin A 9-O-tropyloxime derivative of formula (III):

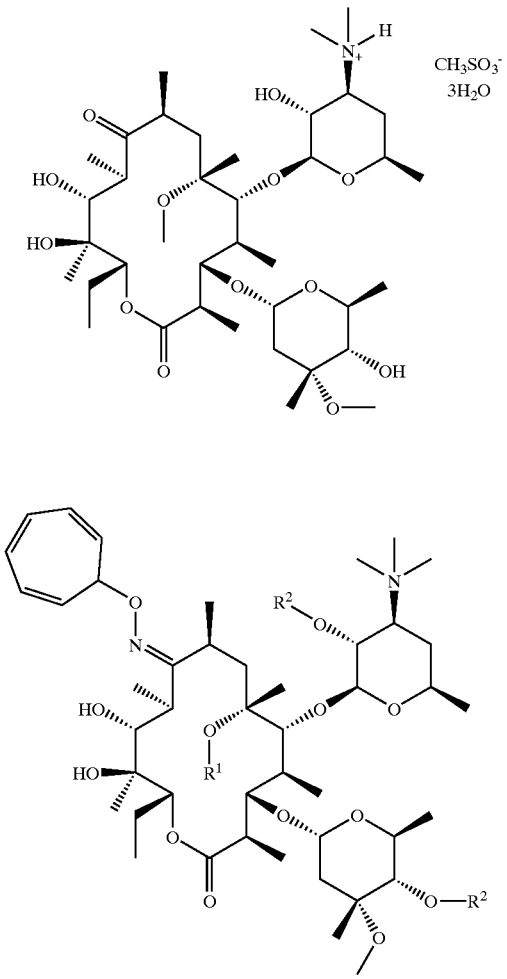

wherein, $R^1$ is hydrogen or methyl group; and $R^2$ is hydrogen or trimethylsilyl group (if $R^1$ is methyl group, $R^2$ is trimethylsilyl group).

BRIEF DESCRIPTION OF THE DRAWINGS

The above and other objects and features of the present invention will become apparent from the following description of the invention taken in conjunction with the following accompanying drawings, wherein.

DETAILED DESCRIPTION OF THE INVENTION

Figure 1:
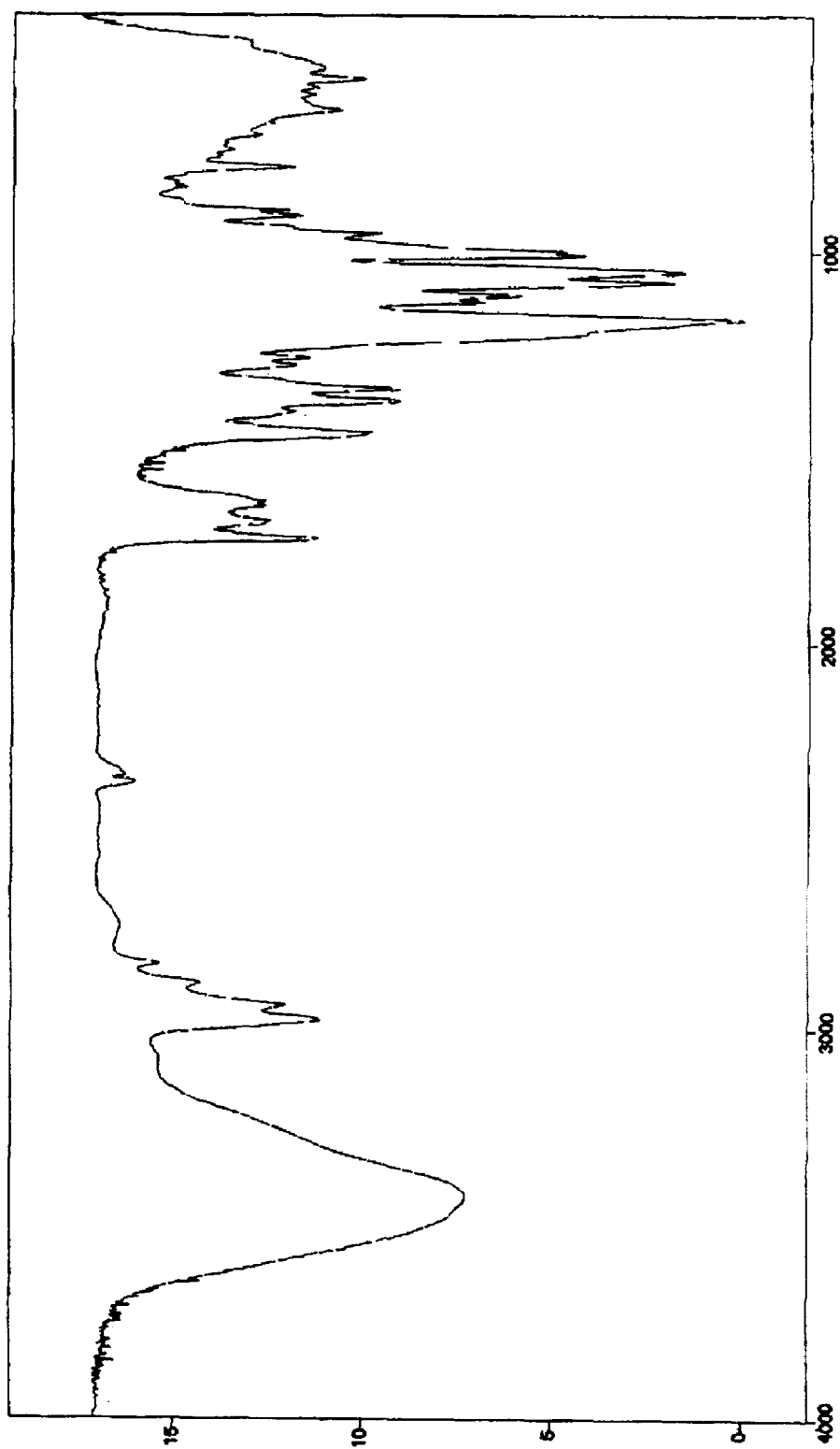
FIGS. 1 and 2 represent the Infrared spectrum and powder X-ray diffraction spectra of clarithromycin mesylate trihydrate, respectively.

The term "non-pharmaceutical grade clarithromycin" as used herein refers to clarithromycin of any purity or of any stage of crystalline, and clarithromycin of crude state obtained from a manufacturing process thereof.

In accordance with the present invention, crystalline clarithromycin mesylate trihydrate of formula (II) is prepared by treating non-pharmaceutical grade clarithromycin obtained with methanesulfonic acid in a mixture of a water-miscible organic solvent and water.

Specifically, feed clarithromycin is dissolved or suspended in a mixture of a water-miscible organic solvent, e.g., acetone, ethanol or isopropanol, and water at a temperature ranging from room temperature to 45□. The solvent mixture contains water in an amount of more than 3 equivalents, preferably 3 to 15 equivalents based on clarithromycin used.

Then, methanesulfonic acid, neat or dissolved in the same solvent mixture, is added to the suspension in an amount ranging from 0.9 to 1.1 equivalents based on the amount of clarithromycin. The mixture may be kept at a temperature in the range of room temperature to 45□ for 30 minutes to 3 hours. The resulting mixture is cooled to a temperature ranging from 0 to 5□ and stirred for 1 to 5 hours. Finally, the crystals formed are filtered, washed with the same solvent mixture and dried at a temperature ranging from room temperature to 45□ to obtain crystalline clarithromycin mesylate trihydrate.

If necessary, the clarithromycin mesylate trihydrate crystals thus obtained may be further purified by recrystallization from the same solvent mixture in a conventional manner.

Clarithromycin mesylate trihydrate obtained above is neutralized with an aqueous ammonia solution in a mixture of a water-miscible organic solvent and water, and Form II crystals of clarithromycin are allowed to recrystallize.

Specifically, clarithromycin mesylate trihydrate is dissolved in a mixture of a water-miscible organic solvent and water at room temperature. Then, the solution is filtered to remove impurities and the filtrate is neutralized to a pH in the range of 9 to 12 by adding aqueous ammonia. The resulting solution is stirred for 30 minutes or more to precipitate crystals. Finally, the precipitated crystals are filtered, washed with the same solvent mixture and dried at a temperature ranging from room temperature to 60□ to obtain of clarithromycin Form II crystals.

The water-miscible organic solvent which may be used in the above process is acetone, ethanol, isopropanol or a mixture thereof.

Water and a water-miscible organic solvent may be mixed in a volume ratio ranging from 30:70 to 70:30.

The method of the present invention is very simple and provides of Form II crystals of clarithromycin in a high yield at a low process cost.

The present invention also provides an improved process for preparing non-pharmaceutical grade clarithromycin, which provides a highly efficient, high-yield method for preparing of Form II crystals of clarithromycin when combined with the above-mentioned process for obtaining Form II crystals of clarithromycin.

The first step of this improved process of preparing non-pharmaceutical grade clarithromycin may be carried out as in scheme 1:

Scheme 1

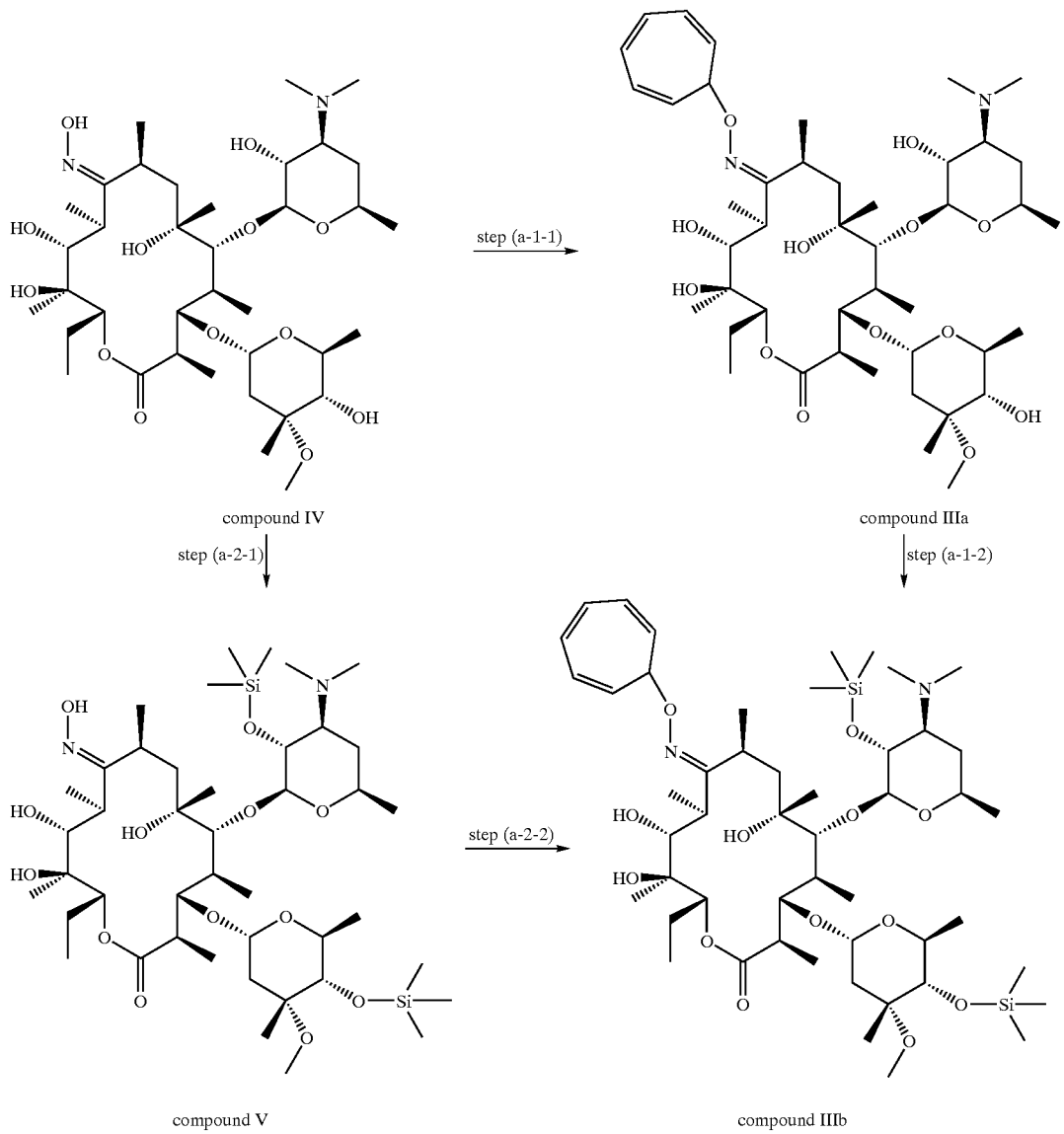

Namely, erythromycin A 9-O-tropyloxime of formula (IIIa) may be produced by reacting erythromycin A 9-oxime of formula (IV) with tropylium tetrafluoroborate in an aprotic polar solvent in the presence of a base at a temperature ranging from 0 to 60□.

Tropylium tetrafluoroborate may be used in an amount ranging from 1 to 1.3 equivalents based on the amount of erythromycin A 9-oxime of formula (IV).

Exemplary aprotic polar solvents which may be suitably used in the above reaction are tetrahydrofuran, 1,4-dioxane, ethyl acetate, acetonitrile, N,N-dimethylformamide, dichloromethane or a mixture thereof and the base may be selected from the group consisting of tertiary amine e.g., triethylamine, tripropylamine, diethylisopropylamine, tributylamine, 1,8-diazabicyclo[5.4.0]undec-7-ene, 1,5-diazabicyclo[4.3.0]non-5-ene and 1,4-diazabicyclo[2.2.2]octane; sodium carbonate; potassium carbonate; sodium hydroxide; potassium hydroxide; potassium t-butoxide; and sodium hydride. The base may be used in an amount ranging from 1 to 1.5 equivalents based on the amount of erythromycin A 9-oxime of formula (IV).

Then, 2',4"-O-bis(trimethylsilyl)erythromycin A 9-O-tropyloxime of formula (IIIb) is produced by reacting erythromycin A 9-O-tropyloxime of formula (IIIa) obtained above with ammonium chloride and 1,1,1,3,3,3,-hexamethyldisilazane in an organic solvent e.g., N,N-dimethylformamide or acetonitrile at a temperature ranging from room temperature to 50□. The amounts of ammonium chloride and 1,1,1,,3,3,3,-hexamethyldisilazane used are in the ranging of 0.5 to 1.5 equivalents and 2 to 4 equivalents, respectively, based on the amount of erythromycin A 9-O-tropyloxime of formula (IIIa).

Alternatively, the compound IIIb may be obtained as follows.

2',4"-O-bis(trimethylsilyl)erythromycin A 9-oxime of formula (V) is produced by reacting erythromycin A 9-oxime of formula (IV) with ammonium chloride and 1,1,1,3,3,3,-hexamethyldisilazane in an organic acid e.g., N,N-dimethylformamide at a temperature ranging from room temperature to 501□. The amounts of ammonium chloride and 1,1,1,,3,3,3,-hexamethyldisilazane used are in the ranging of 0.5 to 1.5 equivalents and 2 to 4 equivalents, respectively, based on the amount of erythromycin A 9-oxime of formula (IV).

Then, 2',4"-O-bis(trimethylsilyl)erythromycin A 9-O-tropyloxime of formula (IIIb) is produced by reacting 2'- and 4"-bis(trimethylsilyl)erythromycin A 9-oxime of formula (V) obtained above with tropylium tetrafluoroborate in an aprotic polar solvent in the presence of a base at a temperature ranging from 0 to 60□. The reaction condition, and the solvent and base used in this reaction may be the same as used in the preparation of formula (IIIa).

As the second step, 2',4"-O-bis(trimethylsilyl)erythromycin A 9-O-tropyloxime of formula (IIIb) obtained in the first steps is methylated with a methylating agent, e.g., methyl iodide in a solvent in the presence of a base to obtain 2',4"-O-bis(trimethylsilyl)-6-O-methylerythromycin A 9-O-tropyloxime of formula (IIIc).

Methyl iodide may be used in an amount ranging from 1 to 1.5 equivalents based on the amount of 2',4"-O-bis(trimethylsilyl)erythromycin A 9-O-tropyloxime of formula (IIIb).

An example of the solvent which may be suitably used in the above reaction is a mixture of tetrahydrofuran and dimethyl sulfoxide having a volume ratio ranging from 2:1 to 1:2.

Exemplary bases that may be suitably used in the above reaction include potassium hydroxide, potassium hydride, potassium t-butoxide, sodium hydride and a mixture thereof. The base may be used in an amount ranging from 1 to 1.3 equivalents based on the amount of 2',4"-O-bis(trimethylsilyl)erythromycin A 9-O-tropyloxime of formula (IIIb). In case potassium hydroxide is used as the base, a potassium hydroxide powder having a particle size of 60 □is preferred.

Finally, 2',4"-O-bis(trimethylsilyl)-6-O-methylerythromycin A 9-O-tropyloxime of formula (IIIc) obtained in the previous step is treated with formic acid and sodium bisulfite in an alcoholic aqueous solution to remove the protecting groups and the oxime group of 2',4"-O-bis(trimethylsilyl)-6-O-methylerythromycin A 9-O-tropyloxime of formula (IIIc) at a temperature ranging from room temperature to the boiling point of the solvent used, to obtain clarithromycin.

The amounts of formic acid and sodium bisulfite used are in the ranging of 1 to 2 equivalents and 2 to 5 equivalents, respectively, based on the amount of 2',4"-O-bis(trimethylsilyl)-6-O-methylerythromycin A 9-O-tropyloxime of formula (IIIc).

Alcoholic aqueous solution which may be suitably used in the above reaction are a mixture of alcohol, e.g., methanol, ethanol and isopropanol, and water in a volume ratio ranging from 2:1 to 1:2.

The above process of preparing non-pharmaceutical grade clarithromycin is much simpler and gives a higher yield of pure product, as compared to the prior art method.

The following Reference Example and Examples are intended to further illustrate the present invention without limiting its scope; and the experimental methods used in the present invention can be practiced in accordance with the Reference Example and Examples given herein below, unless otherwise stated.

Further, percentages given below for solid in solid mixture, liquid in liquid, and solid in liquid are on the bases of wt/wt, vol/vol and wt/vol, respectively, unless specifically indicated otherwise.

REFERENCE EXAMPLE

Preparation of Erythromycin A 9-oxime 31.9 g of erythromycin A was dissolved in 50 □ of methanol. Added thereto were 15.1 g of hydroxylamine-HCl and 15.1 □ of triethylamine and refluxed for 24 hours. The resulting solution was cooled to less than 5□ and stirred for 2 hours. The crystals formed were filtered, washed with cold methanol and dried to give 32.8 g of erythromycin A 9-oxime-HCl in a yield of 96%.

Erythromycin A 9-oxime-HCl obtained above was suspended in 100 □ of methanol, and 20 □ of concentrated aqueous ammonia was added thereto. The resulting solution was stirred at room temperature for 30 minutes and 125 □ of water was added thereto. The resulting solution was stirred at a temperature ranging from 0 to 5□ for several hours. Then, the solids formed were filtered, washed with water and dried to give 26.0 g of the title compound in a yield of 80%.

EXAMPLE 1

Preparation of Erythromycin A 9-O-tropyloxime [Step (a-1-1)]

11.23 g of erythromycin A 9-oxime obtained in Reference Example was dissolved in 75 □ of N,N-dimethylformamide. Added thereto were 3.20 g of tropylium tetrafluoroborate and 3.14 □ of triethylamine, and the mixture was stirred at a temperature ranging from 30 to 40 □ for 4 hours. The resulting solution was cooled to room temperature and 200□ of water was added thereto, and then, extracted twice with 100□ of ethyl acetate. The organic layers were combined and washed twice with water, dried over magnesium sulfate and concentrated under a reduced pressure to give 12.6 g of foamy erythromycin A 9-O-tropyloxime in a yield of 100%, which was recrystallized using acetonitrile to give 10.95 g of the title compound as a white powder in a yield of 87%.

m.p.: 120–122□

$^1$H-NMR (CDCl$_3$, ppm): δ6.68(m, 2H, tropyl 4'''-H and 5'''-H), 6.32(m, 2H, tropyl 3'''-H and 6'''-H), 5.67(m, 2H, tropyl 2'''-H and 7'''-H), 5.12(dd, 1H, 13-H), 4.93(d, 1H, 1''-H), 4.56(t, 1H, tropyl 1'''-H), 4.43(d, 1H, 1'-H), 4.07(dd, 1H, 3-H), 4.02(dq, 1H, 5''-H), 3.67(d, 1H, 11-H), 3.57(d, 1H, 5-H), 3.50(ddq, 1H, 5'-H), 3.49(dq, 1H, 10-H), 3.33(s, 3H, cladinose 3''-OCH$_3$), 3.25(dd, 1H, 2'-H), 3.04(dd, 1H, 4''-H), 2.92(ddq, 1H, 8-H), 2.65(dq, 1H, 2-H), 2.45(ddd, 1H, 3'-H), 2.38(dd, 1H, 2''-H$_{eq}$), 2.30(d, 6H, desosamine 3'-N(CH$_3$)$_2$), 2.23(ddq, 1H, 4-H), 2.03□1.45(m, 6H, 4'-H$_{eq}$, 7-H$_2$, 2''-H$_{ax}$ and 14-H$_2$), 1.43(s, 3H, 18-H), 1.32(d, 3H, 6''-H), 1.26(s, 3H, 7''-H), 1.21□1.02(m, 19H, 4'-H$_{ax}$, 6'-H$_3$, 16-H$_3$, 20-H$_3$, 21-H$_3$, 17-H$_3$ and 19-H$_3$), 0.85(t, 3H, 15-H$_3$).

$^{13}$C-NMR (CDCl$_3$, ppm): δ175.5(C9), 172.9(C1), 131.4 and 131.5(tropyl C4''' and C5'''), 125.2 and 125.4(tropyl C3''' and C6'''), 124.4 and 125.5(tropyl C2''' and C7'''), 103.4 (C1'), 96.7(C1''), 83.6(C5), 80.4(C6), 78.5(C3), 78.1(tropyl C1'''), 77.3(C4''), 75.7(C13), 74.7(C12), 73.1(C3''), 71.4 (C2'), 71.0(C11), 69.2(C5'), 66.0(C5''), 65.9(C3'), 49.9 (C8''), 45.1(C2), 40.7(C7' and C8'), 39.4(C4), 38.2(C7), 35.5(C2''), 33.4(C8), 29.1(C4'), 27.3(C10), 26.8(C19), 21.9 (C6'), 21.8(C7''), 21.5(C14), 19.1(C18), 19.1(6''), 16.6 (C21), 16.5(C16), 14.9(C20), 11.0(C15), 9.5(C17).

EXAMPLE 2

Preparation of Erythromycin A 9-O-tropyloxime [Step (a-1-1)]

The procedure of Example 1 was repeated except that 3.11 g of potassium carbonate was used instead of triethylamine, to give 10.7 g of the title compound as a white powder in a yield of 85%.

Physicochemical and $^1$H-NMR data of this product were identical with those of the compound prepared in Example 1.

EXAMPLE 3

Preparation of Erythromycin A 9-O-tropyloxime [Step (a-1-1)]

11.23 g of erythromycin A 9-oxime obtained in Reference Example was dissolved in 75 □ of N,N-dimethylformamide and cooled to 0 □. Added thereto was 2.19 g of potassium t-butoxide, and the mixture was stirred for 15 minutes. Then, 3.20 g of tropylium tetrafluoroborate was added thereto and stirred at a temperature ranging from 0 to 5 □ for 2 hours, followed by repeating the procedure of Example 1 to give 11.33 g of the title compound as a white powder in a yield of 90%.

Physicochemical and $^1$H-NMR data of this product were identical with those of the compound prepared in Example 1.

EXAMPLE 4
Preparation of Erythromycin A 9-O-tropyloxime [Step (a-1-1)]

The procedure of Example 3 was repeated except that tetrahydrofuran was used instead of N,N-dimethylformamide and that the reaction was carried out for 3 hours, to give 11.46 g of the title compound as a white powder in a yield of 91%.

Physicochemical and $^1$H-NMR data of this product were identical with those of the compound prepared in Example 1.

EXAMPLE 5
Preparation of Erythromycin A 9-O-tropyloxime [Step (a-1-1)]

11.23 g of erythromycin A 9-oxime obtained in Reference Example was dissolved in 120 □ of acetonitrile. Added thereto was 3.20 g of tropylium tetrafluoroborate, and then, 3.14 □ of triethylamine was added dropwise thereto while maintaining the temperature at 30 to 40□. The resulting solution was stirred at the same temperature for 4 hours and cooled to 0□ and then, stirred for 1 hour. The solids formed were filtered, washed with cold acetonitrile and dried to give 11.83 g of the title compound as a white powder in a yield of 94%.

Physicochemical and $^1$H-NMR data of this product were identical with those of the compound prepared in Example 1.

EXAMPLE 6
Preparation of 2',4"-O-bis(trimethylsilyl)erythromycin A 9-O-tropyloxime [Step (a-1-2)]

12.59 g of erythromycin A 9-O-tropyloxime obtained in Example 1 was dissolved in 75 □ of N,N-dimethylformamide. Added thereto were 1.20 g of ammonia chloride and 6.3□ of 1,1,1,3,3,3-hexamethyldisilazane, and the mixture was stirred at a temperature ranging from 35 to 40□ for 4 hours. The resulting solution was cooled to room temperature and 200□ of water was added thereto and then, extracted twice with 100□ of ethyl acetate. The organic layers were combined and washed twice with water, dried over magnesium sulfate and concentrated under a reduced pressure to give 14.5 g of foamy 2',4"-O-bis(trimethylsilyl)erythromycin A 9-O-tropyloxime in a yield of 98%.

$^1$H-NMR (CDCl$_3$, ppm): δ6.68(m, 2H, tropyl 4'"-H and 5'"-H), 6.30(m, 2H, tropyl 3'"-H and 6'"-H), 5.66(m, 2H, tropyl 2'"-H and 7'"-H), 5.10(dd, 1H, 13-H), 4.90(d, 1H, 1"-H), 4.53(t, 1H, tropyl 1'"-H), 4.40(d, 1H, 1'-H), 4.25(dq, 1H, 5"-H), 4.19(dd, 1H, 3-H), 3.69(d, 1H, 11-H), 3.66(ddq, 1H, 5'-H), 3.62(dq, 1H, 10-H), 3.58(d, 1H, 5-H), 3.32(s, 3H, cladinose 3"-OCH$_3$), 3.18(dd, 1H, 2'-H), 3.16(dd, 1H, 4"-H), 2.85(ddq, 1H, 8-H), 2.70(dq, 1H, 2-H), 2.55(ddd, 1H, 3'-H), 2.39(dd, 1H, 2"-H$_{eq}$), 2.25(d, 6H, desosamine 3'-N(CH$_3$)$_2$), 2.00□1.40(m, 7H, 4-H, 4'-H$_{eq}$, 7-H$_2$, 2"-H$_{ax}$ and 14-H$_2$), 1.42(s, 3H, 18-H), 1.21(d, 3H, 6"-H), 1.18(s, 3H, 7"-H), 1.25□0.99(m, 19H, 4'-H$_{ax}$, 6'-H$_3$, 16-H$_3$, 20-H$_3$, 21-H$_3$, 17-H$_3$ and 19-H$_3$), 0.87(t, 3H, 15-H$_3$) 0.16(s, 9H, 4"-OSi (CH$_3$)$_3$), 0.11(s, 9H, 2'-OSi(CH$_3$)$_3$).

$^{13}$C-NMR (CDCl$_3$, ppm): δ176.1(C9), 172.6(C1), 131.6 and 131.3(tropyl C4'" and C5'"), 125.2 and 125.0(tropyl C3'" and C6'"), 124.7 and 124.7(tropyl C2'" and C7'"), 103.1 (C1'), 97.0(C1"), 81.8(C5), 81.3(C6), 79.8(C3), 78.2(and C1'"), 77.3(C4"), 75.9(C13), 74.7(C12), 73.7(C3"), 73.6 (C2'), 71.0(C11), 68.1(C5'), 65.5(C5"), 65.3(C3'), 50.1 (C8"), 45.1(C2), 41.4(C7' and C8'), 40.3(C4), 38.9(C7), 36.3(C2"), 33.5(C8), 30.1(C4'), 27.4(C10), 26.8(C19), 22.6 (C6'), 22.2(C7"), 21.6(C14), 19.8(C18), 19.0(6"), 16.6 (C21), 16.2(C16), 14.8(C20), 11.1(C15), 10.0(C17). 1.41 (4"-OSi(CH$_3$)$_3$), 1.31(2'-OSi(CH$_3$)$_3$).

EXAMPLE 7
Preparation of 2',4"-O-bis(trimethylsilyl)erythromycin A 9-O-tropyloxime from erythromycin A 9-oxime [steps (a-1-1) and (a-1-2)]

11.23 g of erythromycin A 9-oxime obtained in Reference Example was dissolved in 75 □ of N,N-dimethylformamide and cooled to 0□. Added thereto was 2.19 g of potassium t-butoxide and the mixture was stirred for 15 minutes. Added thereto was 3.20 g of tropylium tetrafluoroborate, and the mixture was stirred at 0 to 5□ for 3 hours. Then, 1.34 g of ammonium chloride and 10. 0□ of 1,1,1,3,3,3-hexamethyldisilazane were added and the mixture was stirred at 35 to 40□ for 4 hours. The resulting solution was cooled to room temperature and 200□ of water was added thereto, and then, extracted twice with 100□ of ethyl acetate. The organic layers were combined and washed twice with water, dried over magnesium sulfate and concentrated under a reduced pressure to give 13.5 g of foamy 2',4"-O-bis(trimethylsilyl)erythromycin A 9-O-tropyloxime in a yield of 90%.

$^1$H-NMR data of this product were identical with those of the compound prepared in Example 6.

EXAMPLE 8
Preparation of 2',4"-O-bis(trimethylsilyl)erythromycin A 9-oxime [step (a-2-1)]

32.8 g of erythromycin A 9-oxime-HCl obtained in Reference Example was dissolved in 125 □ of N,N-dimethylformamide. Added thereto were 1.13 g of ammonium chloride and 23□ of 1,1,1,3,3,3-hexamethyldisilazane, and the mixture was stirred at 40 to 45□ for 2 hours. 15□ of 4N-sodium hydroxide, 100□ of water and 50□ of hexane were added stepwise thereto and the mixture was stirred for 2 hours. The solids formed were filtered to give 31.4 g of 2',4"-O-bis(trimethylsilyl)erythromycin A 9-oxime in a yield of 81%.

EXAMPLE 9
Preparation of 2',4"-O-bis(trimethylsilyl)erythromycin A 9-O-tropyloxime [step (a-2-2)]

8.93 g of 2',4"-O-bis(trimethylsilyl)erythromycin A 9-oxime obtained in Example 8 was dissolved in 40□ of tetrahydrofuran and cooled to 0□. Added thereto was 0.52 g of 60% sodium hydride, and the mixture was stirred for 20 minutes. Then, 2.14 g of tropylium tetrafluoroborate was added thereto and stirred at 0 to 5□ for 3 hours, followed by repeating the procedure of Example 6 to give 9.44 g of 2',4"-O-bis(trimethylsilyl)erythromycin A 9-O-tropyloxime as a white foam in a yield of 96%.

$^1$H-NMR data of this product were identical with those of the compound prepared in Example 6.

EXAMPLE 10
Preparation of 2',4"-O-bis(trimethylsilyl)erythromycin A 9-O-tropyloxime [Step (a-2-2)]

13.4 g of 2',4"-O-bis(trimethylsilyl)erythromycin A 9-oxime obtained in Example 8 and 2.67 g of tropylium tetrafluoroborate were dissolved in 50□ of dichloromethane at room temperature. Then, 2.3□ of triethylamine was added thereto and stirred at the same temperature for 3 hours, followed by adding water. The organic layers were combined and washed with water, dried over magnesium sulfate and concentrated under a reduced pressure to give 14.6 g of foamy 2',4"-O-bis(trimethylsilyl)erythromycin A 9-O-tropyloxime in a yield of 99%.

¹H-NMR data of this product were identical with those of the compound prepared in Example 6.

EXAMPLE 11

Preparation of 2',4"-O-bis(trimethylsilyl)-6-O-methylerythromycin A 9-O-tropyloxime 14.75 g of 2',4"-O-bis(trimethylsilyl)erythromycin A 9-O-tropyloxime obtained in the previous Examples was dissolved in a mixture of 60□ of tetrahydrofuran and 60□ of dimethyl sulfoxide and cooled to 0□. Added thereto were 1.21 □ of methyl iodide and 1.09 g of 85% potassium hydroxide. Then, the mixture was stirred at 0 to 5□ for 4 hours. 150□ of water was added thereto and extracted twice with 100□ of ethyl acetate. The organic layers were combined and washed twice with water, dried over magnesium sulfate, and then, concentrated under a reduced pressure to give 14.71 g of foamy 2',4"-O-bis(trimethylsilyl)-6-O-methylerythromycin A 9-O-tropyloxime in a yield of 98%.

¹H-NMR (CDCl₃, ppm): δ6.65(m, 2H, tropyl 4'"-H and 5'"-H), 6.17(m, 2H, tropyl 3'"-H and 6'"-H), 5.61(m, 2H, tropyl 2'"-H and 7'"-H), 5.11(dd, 1H, 13-H), 4.91(d, 1H, 1'"-H), 4.57(t, 1H, tropyl 1'"-H), 4.43(d, 1H, 1'-H), 4.23(dq, 1H, 5"-H), 4.16(dd, 1H, 3-H), 4.16(d, 1H, 11-H), 3.80(ddq, 1H, 5'-H), 3.68(dq, 1H, 10-H), 3.64(d, 1H, 5-H), 3.34(s, 3H, cladinose 3"-OCH₃), 3.09(s, 3H, 6-OCH₃), 3.19(dd, 1H, 2'-H), 3.16(dd, 1H, 4"-H), 2.87(ddq, 1H, 8-H), 2.60(dq, 1H, 2-H), 2.59(ddd, 1H, 3'-H), 2.38(dd, 1H, ²"-H$_{eq}$), 2.25(d, 6H, desosamine 3'-N (CH₃)₂), 2.00□11.41(m, 7H, 4-H, 4'-H$_{eq}$, 7-H₂, 2"-H$_{ax}$ and 14-H₂), 1.46(s, 3H, 18-H), 1.28(d, 3H, 6"-H), 1.18(s, 3H, 7"-H), 1.22□10.95(m, 19H, 4'-H$_{ax}$, 6'-H₃, 16-H₃, 20-H₃, 21-H₃, 17-H₃ and 19-H₃), 0.85(t, 3H, 15-H₃), 0.16(s, 9H, 4"-OSi(CH₃)₃), 0. 11(s, 9H, 2-OSi(CH₃)₃).

¹³C-NMR (CDCl₃, ppm): δ176.3(C9), 171.4(C1), 131.4 and 131.4(tropyl C4'" and C5"), 126.0 and 125.1(tropyl C3'" and C6'"), 123.4 and 123.1(tropyl C2'" and C7'"), 103.0 (C1'), 96.6(C1"), 81.3(C5), 79.4(C6), 79.3(tropyl C1'"), 78.4 (C3), 77.1(C4"), 77.0(C13), 74.3(C12), 73.7(C3"), 73.6 (C2'), 71.5(C11), 67.6(C5'), 65.5(C5"), 65.5(C3'), 51.5(6-OCH₃), 50.1(C8"), 45.8(C2), 41.4(C7' and C8'), 40.0(C4), 38.2(C7), 36.2(C2"), 33.4(C8), 30.0(C4'), 26.7(C10), 22.6 (Cl9), 21.6(C6'), 22.4(C7"), 20.6(C14), 19.8(C18), 19.1(6"), 16.6(C21), 16.5(C16), 15.5(C20), 11.1(C15), 10.1(C17). 1.46(4"-OSi(CH₃)₃), 1.29(2'-OSi(CH₃)₃).

EXAMPLE 12

Preparation of 2',4"-O-bis(trimethylsilyl)-6-O-methylerythromycin A 9-O-tropyloxime from 2',4"-O-bis(trimethylsilyl)erythromycin A 9-oxime 8.93 g of 2',4"-O-bis(trimethylsilyl)erythromycin A 9-oxime obtained in Example 8 was dissolved in 40□ of tetrahydrofuran and cooled to 0□. Added thereto was 1.46 g of potassium t-butoxide, and the mixture was stirred for 20 minutes. Then, 2.14 g of tropylium tetrafluoroborate was added thereto and stirred at 0 to 5□ for 3 hours. 40□ of dimethyl sulfoxide, 0.81□ of methyl iodide and 0.73 g of 85% potassium hydroxide powder were added to the mixture and stirred at 0 to 5□ for 4 hours.

Then, the work-up procedure of Example 11 were repeated to give 9.27 g of 2',4"-O-bis(trimethylsilyl)-6-O-methylerythromycin A 9-O-tropyloxime as a white foam in a yield of 93%.

¹H-NMR data of this product was identical with those of the compound prepared in Example 11.

Test Example

The crude products obtained in the above methylation steps of the 6-hydroxy group of 2',4"-O-bis(trimethylsilyl) erythromycin A 9-O-tropyloxime were analyzed in HPLC to determine the selectivity for 6-O-methylation and compared with those obtained in the corresponding steps of the prior art, and the results are shown in Table 1.

TABLE 1

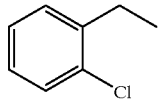

| (R) | reaction product ratio(%) | | | |
|---|---|---|---|---|
| | 6-OMe | 6,11-diOMe | 6-OH | the others |
| EP Patent No. 260,938 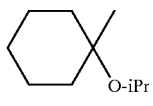 | 84.8 | 4.8 | 7.0 | 3.4 |
| U.S. Pat. No. 4,990,602-1 | 87.2 | 2.3 | 4.0 | 6.5 |
| U.S. Pat. No. 4,990,602-2 | 90.0 | 1.0 | 5.5 | 3.5 |
| the present invention 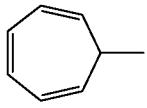 | 92.8 | <1.0 | 3.5 | 2.7 |

As the above results show, 2',4"-O-bis(trimethylsilyl) erythromycin A 9-O-tropyloxime of the present invention give the highest selectivity to the methylation of the 6-hydroxy group.

EXAMPLE 13

Preparation of Clarithromycin 13.3 g of 2',4"-O-bis(trimethylsilyl)-6-O-methylerythromycin A 9-O-tropyloxime obtained in Example 11 was dissolved in 70□ of ethanol. 0.75 □ of formic acid, 70□ of water and 4.16 g of sodium bisulfite were added stepwise thereto and the mixture was refluxed for 2 hours. The resulting solution was cooled to below 10□ and 140 □ of water and 50□ of hexane were added thereto. The resulting solution was adjusted to pH 10 by adding 2N-sodium hydroxide. The mixture was stirred at below 10□ for 1 hour and the solids formed were filtered, washed with water, and then, dried at about 50□ to give 7.46 g of crude clarithromycin as a white powder in a yield of 75%.

m.p.: 220□223□ (e.g., m.p. in literature for Form I Crystals, 222□225□).

$^1$H-NMR (CDCl$_3$, ppm): δ5.06(dd, 1H, 13-H), 4.92(d, 1H, 1"-H), 4.44(d, 1H, 1'-H), 4.02(dq, 1H, 5"-H), 3.78(dd, 1H, 3-H), (dq, 1H, 5"-H), 3.77(d, 1H, 11-H), 3.67(d, 1H, 5-H), 3.57(ddq, 1H, 5'-H), 3.33(s, 3H, 3"-OCH$_3$), 3.20(dd, 1H, 2'-H), 3.04(s, 3H, 6-OCH$_3$), 3.03(dd, 1H, 4"-Hz), 2.99 (dq, 1H, 10-H), 2.87(dq, 1H, 2-H), 2.58(ddq, 1H, 8-H), 2.40(ddd, 1H, 3'-H), 2.37(d, 1H, 2"-H$_{eq}$), 2.28(s, 6H, 3'-N(CH$_3$)$_2$), 2.00□1.80(m, 3H, 4-H, 7-H$_2$, 14-H$_1$), 1.75LP 1.40(m, 3H, 4'-Heq, 2"-H$_{ax}$ and 14-H$_1$), 1.41(s, 3H, 18-H), 1.13(s, 3H, 6-CH$_3$), 1.31(d, 3H, 6"-H$_3$), 1.30□1.05(m, 22H, 7"-H$_3$, 4'-H$_{ax}$, 6'-H$_3$, 16-H$_3$, 20-H$_3$, 21-H$_3$, 17-H$_3$ and 19-H$_3$), 0.84(t, 3H, 15-H$_3$).

$^{13}$C-NMR (CDCl$_3$, ppm): δ221.0(C9), 175.9(C1), 102.8 (C1'), 96.0(C1"), 80.7(C5), 78.4(C6), 78.4(C4"), 77.9(C3), 76.6(C13), 74.2(C12), 72.6(C3"), 70.9(C2'), 69.0(C11), 68.7 (C5'), 65.8(C5"), 65.5(C3'), 50.6(6-OCH$_3$), 49.4(C8"), 45.2 (C8), 45.0(C2), 40.2(C7' and C8'), 39.4(C7), 39.3(C4), 37.2 (C10), 34.8(C2"), 28.5(C4'), 21.4(C6'), 21.4(C7"), 21.0 (C14), 19.7(C18), 18.6(6"), 17.9(C19), 15.9(C21), 15.9 (C16), 12.2(C20), 10.6(C15), 9.0(C17).

7"-H), 1.23 (d, 3H, 6'-H), 1.21 (d, 3H, 16-H), 1.14 (d, 3H, 19-H), 1.13 (d, 3H, 20-H), 1.12 (s, 3H, 21-H), 1.09 (d, 3H, 17-H), 0.83 (t, 3H, 15-CH$_3$).

$^{13}$C-NMR (CDCl$_3$, ppm): δ221.3 (9-C), 176.4 (1-C), 102.4 (1'-C), 97.0 (1"-C), 82.3 (5-C), 79.5 (3-C), 78.9 (6-C), 78.3 (4"-C), 77.4 (13-C), 74.9 (12-C), 73.6 (3"-C), 70.6 (2'-C), 69.7 (11-C), 67.7 (5'-C), 66.7 (5"-C), 66.1 (3'-C), 51.1 (22-C), 49.9 (8"-C), 45.7 (8-C), 45.6 (2-C), 39.8 (7'-C, 8'-C and 7-C), 39.7 (4-C), 38.0 (10-C), 35.7 (2"-C), 31.6 (4'-C), 22.0 (6'-C), 21.6 (7"-C and 14-C), 20.5 (18-C), 19.2 (6"-C), 18.5 (19-C), 16.7 (21-C), 16.5 (16-C), 12.8 (20-C), 11.2 (15-C), 9.9 (17-C).

The above procedure was repeated using less pure clarithromycin batches and the results are summarized in Table 2.

Figure 2:
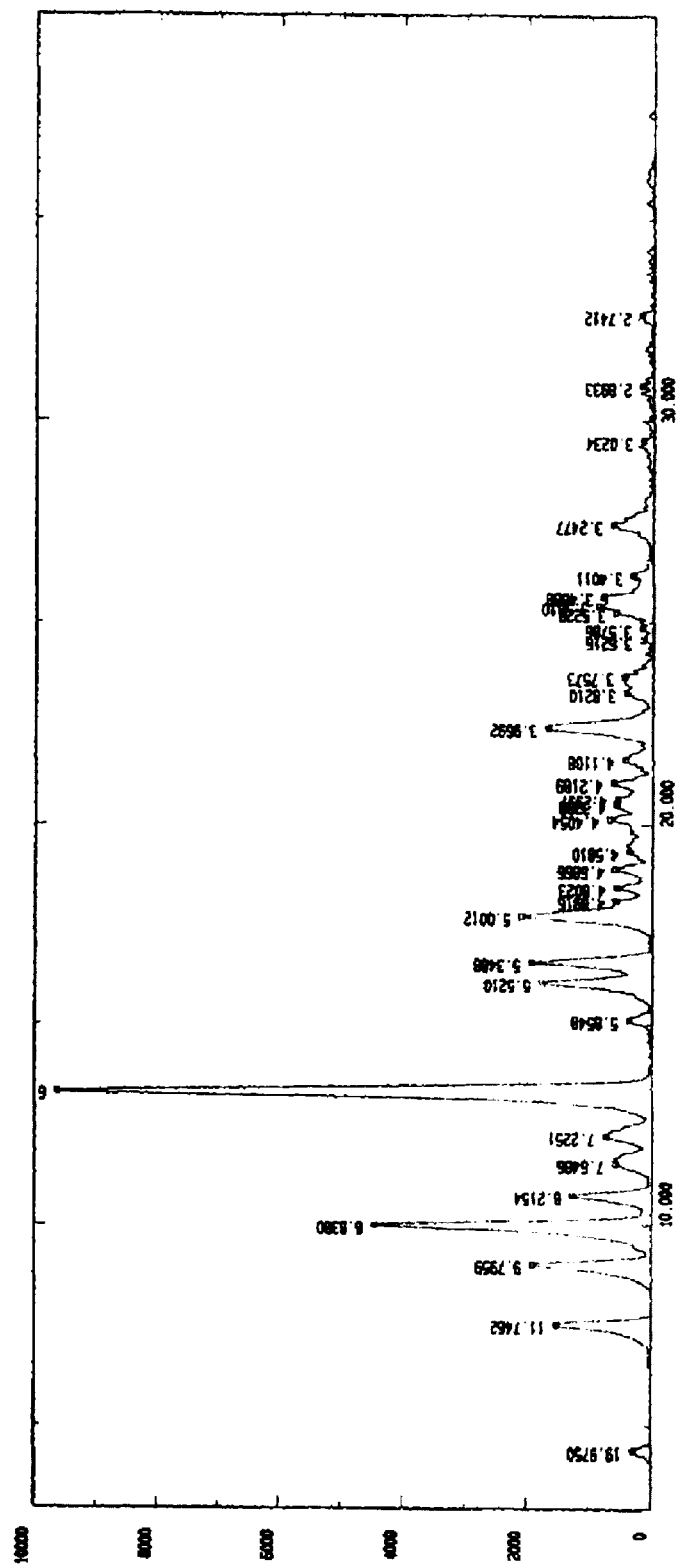

The Infrared and powder X-ray diffraction spectra of clarithromycin mesylate trihydrate are shown in FIGS. 1 and 2, respectively.

EXAMPLE 15 and 16

Preparation of Clarithromycin Mesylate Trihydrate

In each of Example 15 and 16, the procedure of Example 14 was repeated except that a different organic solvent was used instead of acetone. The results are shown in Table 2.

TABLE 2

| | Organic solvent | | Purity(%) | | Amount | Yield | Moisture |
|---|---|---|---|---|---|---|---|
| | Ingredient | Volume (□) | A | B | (g) | (%) | (%) |
| Ex. 14 | 95% acetone | 32 | 97.0 | 98.8 | 12.4 | 92 | 6.2 |
| | | | 94.4 | 97.2 | 11.7 | 87 | 6.1 |
| | | | 90.2 | 96.0 | 11.0 | 82 | 6.3 |
| Ex. 15 | 95% ethanol | 40 | 97.0 | 98.1 | 11.8 | 88 | 6.0 |
| | | | 94.4 | 97.5 | 11.3 | 84 | 6.1 |
| | | | 90.2 | 96.5 | 10.8 | 80 | 6.4 |
| Ex. 16 | 95% isopropanol | 40 | 97.0 | 98.0 | 12.0 | 89 | 6.1 |
| | | | 94.4 | 97.3 | 11.6 | 86 | 6.3 |
| | | | 90.2 | 97.3 | 11.2 | 83 | 6.3 |

A: Clarithromycin used
B: Clarithromycin mesylate trihydrate obtained

EXAMPLE 14

Preparation of Clarithromycin Mesylate Trihydrate 11.2 g of clarithromycin(15 mmol) having a purity of 97% was dissolved in 32□ of 95% acetone, and methanesulfonic acid was added dropwise thereto, and then, stirred at room temperature for 1 hour. Then, the suspension was cooled to OF and stirred for 3 hours. The crystals formed were filtered, washed with cold acetone and dried at 45□ to give 10.3 g of crystalline clarithromycin mesylate trihydrate (purity: 98.8% and yield: 92%).

m.p.: 160□161□ moisture content: 6.2% (Karl Fischer, theoretical moisture content for trihydrate: 6.02%)

IR (KBr, cm$^{-1}$): 3428, 2978, 2939, 1734, 1686, 1459, 1378, 1347, 1170, 1110, 1077, 1051, 1010, 954, 908, 892, 780.

$^1$H-NMR (CDCl$_3$, ppm): δ5.07 (dd, 1H, 13-H), 4.91 (d, 1H, 1"-H), 4.60 (d, 1H, 1'-H), 3.98 (dq, 1H, 5"-H), 3.76 (ddq, 1H, 5'-H), 3.76 (d, 1H, 1-H), 3.72 (dd, 1H, 3-H), 3.70 (dd, 1H, 5-H), 3.55 (ddd, 1H, 3'-H), 3.47 (dq, 1H, 2'-H), 3.35 (s, 3H, 3"-OCH$_3$), 3.07 (dd, 1H, 4"-H), 3.04 (s, 3H, 6-OCH$_3$), 3.03 (s, 1H, 10-H), 2.93 (s, 6H, 3'-N(CH$_3$)$_2$), 2.87 (dq, 1H, 8-H), 2.78 (s, 3H, CH$_3$SO$_3^-$), 2.58 (dq, 1H, 2-H), 2.37 (dd, 1H, 2"-H$_{eq}$), 2.08 (ddd, 1H, 4'-H$_{eq}$), 1.94 (ddq, 1H, 4-H), 1.93 (dd, 1h, 7-H$_{ax}$), 1.92 and 1.48 (ddq, 2H, 14-H), 1.72 (dd, 1H, 7-H$_{eq}$), 1.59 (ddq, 1H, 2"-Hax), 1.41 (s, 3H, 18-H), 1.31 (d, 3H, 6"-H), 1.30 (ddd, 1H, 4'-H$_{ax}$), 1.25 (s, 3H,

EXAMPLES 17

Recrystallization of Clarithromycin Mesylate Trihydrate 14.0 g of clarithromycin mesylate trihydrate having a purity of 92% was suspended in 50□ of 95% ethanol, refluxed to dissove completely, cooled to 0□, and stirred for 4 hours. Then, the crystals formed were filtered, washed with acetone chilled to 0F and dried at 45□ to give 12.0 g of refined crystalline clarithromycin mesylate trihydrate (purity: 97.5%, recovery: 86% and moisture content: 6.2%).

EXAMPLES 18

Recrystallization of Clarithromycin Mesylate Trihydrate

The procedure of Example 17 was repeated except that 95% isopropanol was used instead of ethanol. The result is shown in Table 3.

TABLE 3

| | Organic solvent | Amount (g) | Recovery (%) | Purity (%) | Moisture content (%) |
|---|---|---|---|---|---|
| Ex. 17 | 95% ethanol | 12.0 | 86 | 97.5 | 6.2 |
| Ex. 18 | 95% isopropanol | 12.2 | 84 | 97.1 | 6.3 |

EXAMPLES 19

Preparation of Form II Crystals of Clarithromycin from Clarithromycin Mesylate Trihydrate 14.0 g of clarithromycin mesylate trihydrate (purity: 96%) was dissolved in a mixture of 42□ of ethanol and 84□ of water, and filtered to remove insoluble ingredients. 4.8□ of concentrated aqueous ammonia was added dropwise to the filtrate and stirred for 3 hours. Then, the crystals formed were filtered and dried overnight under an air at 55□ to give 11.3 g of Form II crystals of clarithromycin (purity: 97.2% and yield: 97%).

Figure 3:
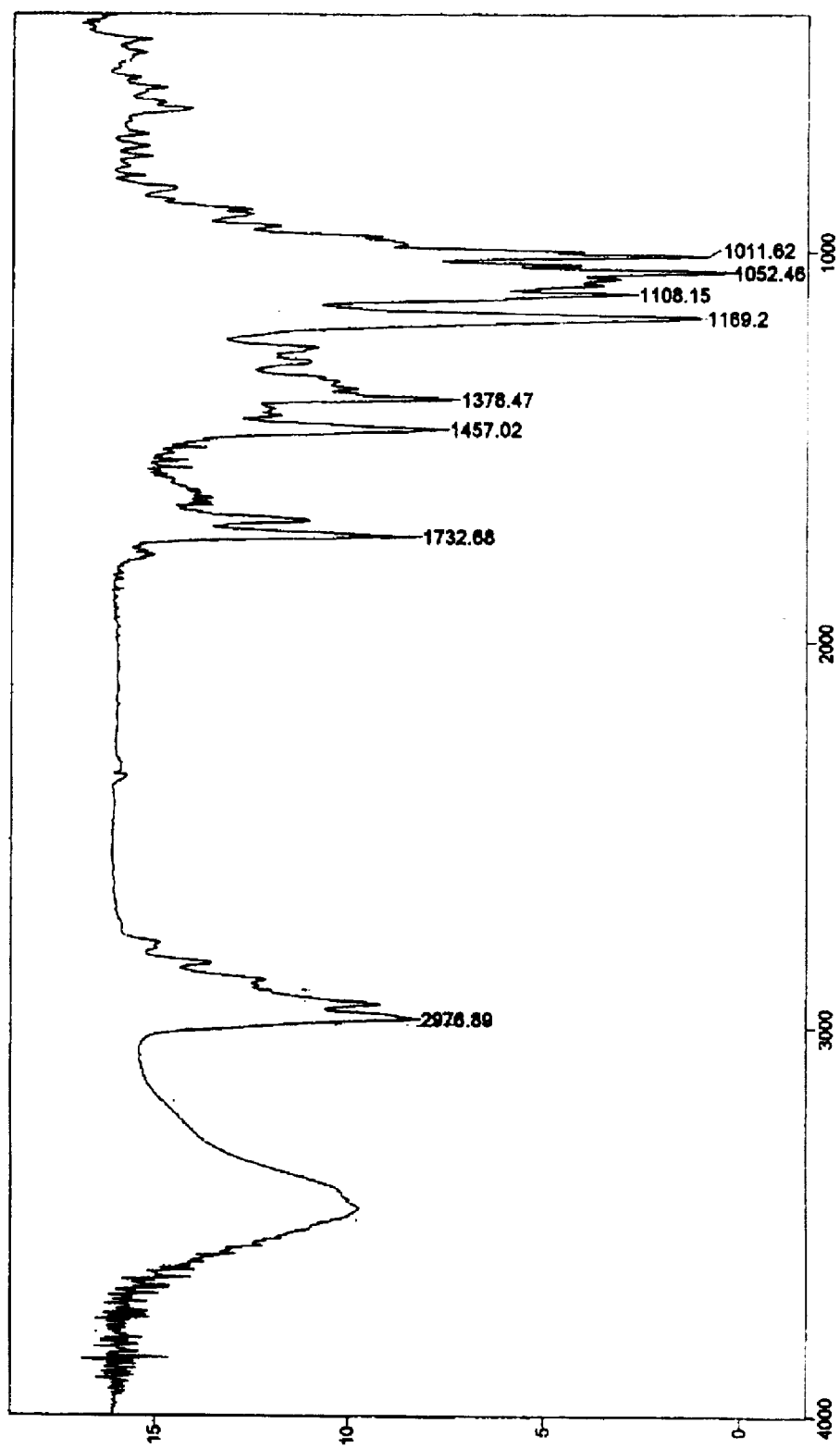
FIGS. 3 and 4 display the Infrared spectrum and powder X-ray diffraction spectra of Form II crystals of clarithromycin, respectively.
Figure 4:
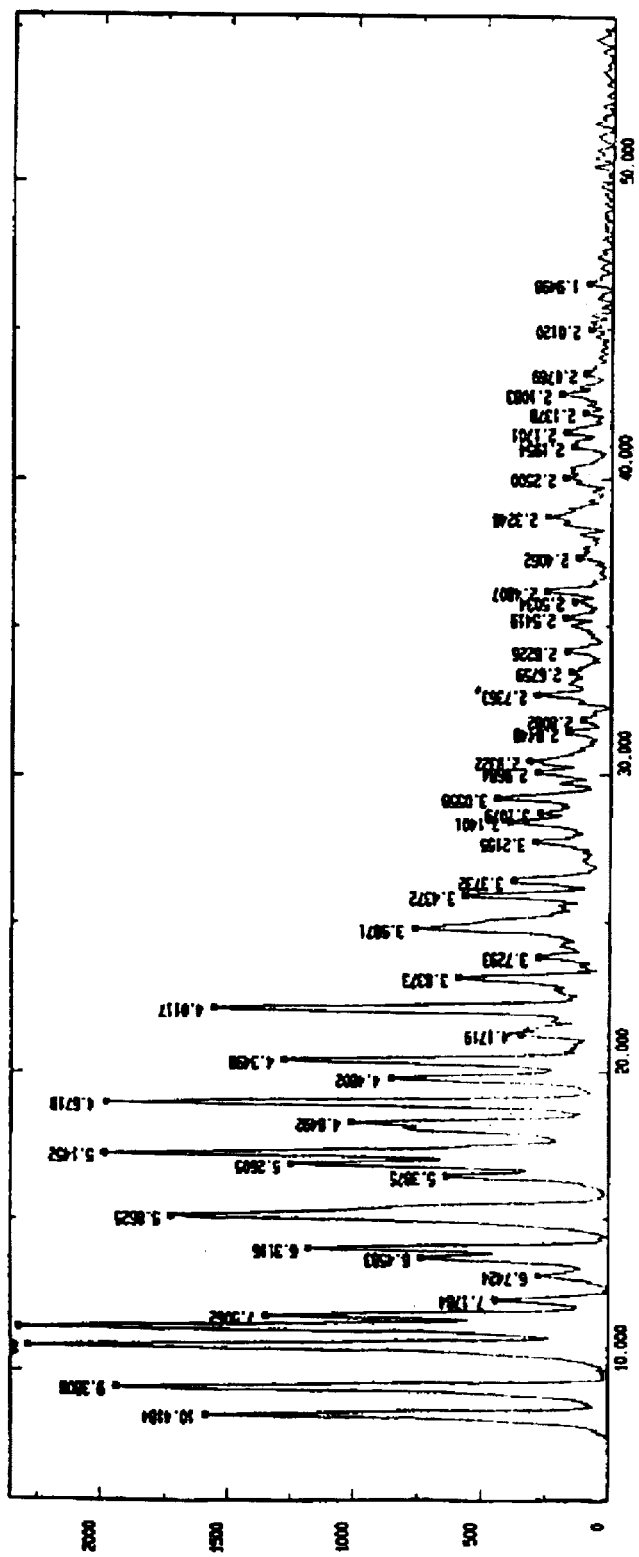

The Infrared and powder X-ray diffraction spectra of Form II crystals of clarithromycin are shown in FIGS. 3 and 4, respectively.

EXAMPLES 20
Preparation of Form II Crystals of Clarithromycin from Crude Clarithromycin 93.1 g of crude clarithromycin (0.124 mol) was dissolved in 260□ of 95% acetone and filtered to remove insoluble ingredients. 10 g of methanesulfonic acid (0.105 mol) was added dropwise thereto and stirred for 1 hour. Then, the suspension obtained was cooled to 0□ and the resulting solution was stirred for 3 hours. The crystals formed were filtered, washed with cold acetone and dried at 45□ to give 87.5 g of crystalline clarithromycin mesylate trihydrate (purity: 93%, yield: 78% and moisture content: 6.4%).

87.5 g of clarithromycin mesylate trihydrate(0.097 mol) was suspended in 306□ of 95% ethanol, refluxed for 30 minutes to dissolve completely, and then, cooled slowly to 0□ while stirring. Then, the mixture was stirred at 0□ for 4 hours and the crystals formed were filtered, washed with acetone chilled to 0□ land dried at 45□ to give 74.4 g of refined crystalline clarithromycin mesylate trihydrate (purity: 97.0%, yield: 85% and moisture content: 6.1%).

74.4 g of clarithromycin mesylate trihydrate (0.083 mol) obtained above was suspended in a mixture of 220□ of ethanol and 440□ of water, and filtered to remove insoluble ingredients. 25□ of concentrated aqueous ammonia was added dropwise to the filtrate and stirred at room temperature for 3 hours. Then, the crystals formed were filtered and dried overnight at 55□ to give 60.0 g of Form II crystals of clarithromycin (purity: 98.0% and yield: 97%).

COMPARATIVE EXAMPLE 93.1 g of crude clarithromycin (0.124 mol) was crystallized from 600□ of ethanol and dried to give 65.2 g of clarithromycin crystal Form I (purity: 94%, yield: 70%) in accordance with the method disclosed in International Publication No. WO 98/04573.

65.2 g of clarithromycin crystal Form I (0.087 mol) was suspended in 510□ of ethanol and refluxed for 1 hour to dissolve most of the crystals. The solution was hot-filtered to remove insoluble ingredients, and the filtrate was cooled to 10□ and stirred for 2 hours. Then, the crystals formed were filtered and dried at 50□ to give 54.1 g of refined clarithromycin crystal Form I (purity: 97.1% and recovery: 83%).

Then, Form II crystals of clarithromycin was produced from clarithromycin crystal Form I in accordance with the method disclosed in International Publication No. WO 98/04574.

That is, 54.1 g of refined clarithromycin crystal Form I (0.072 mol) was suspended in 2701□ of ethyl acetate and refluxed for 1 hour. Insoluble ingredients were removed by hot-filtration, and 40□ of ethyl acetate was added to the filtrate and refluxed. The solution was cooled to 50□, and 270□ of isopropyl ether was added thereto and cooled to 5□. The resulting crystals were filtered and dried to give 41.7 g of Form II crystals of clarithromycin (purity: 97.2% and yield: 77%).

While the embodiments of the subject invention have been described and illustrated, it is obvious that various changes and modifications can be made therein without departing from the spirit of the present invention which should be limited only by the scope of the appended claims.

What is claimed is:

1. A method of preparing Form II crystals of clarithromycin of formula (I) comprising the steps of:

(a) treating non-pharmaceutical grade clarithromycin with methanesulfonic acid in a mixture of a water-miscible organic solvent and water to obtain crystalline clarithromycin mesylate trihydrate of formula (II); and (b) neutralizing the crystalline clarithromycin mesylate trihydrate obtained step (a) with aqueous ammonia in a mixture of a water-miscible organic solvent and water; wherein non-pharmaceutical grade clarithromycin refers to clarithromycin of any purity or of any stage of crystalline, and crude clarithromycin obtained from a manufacturing process thereof:

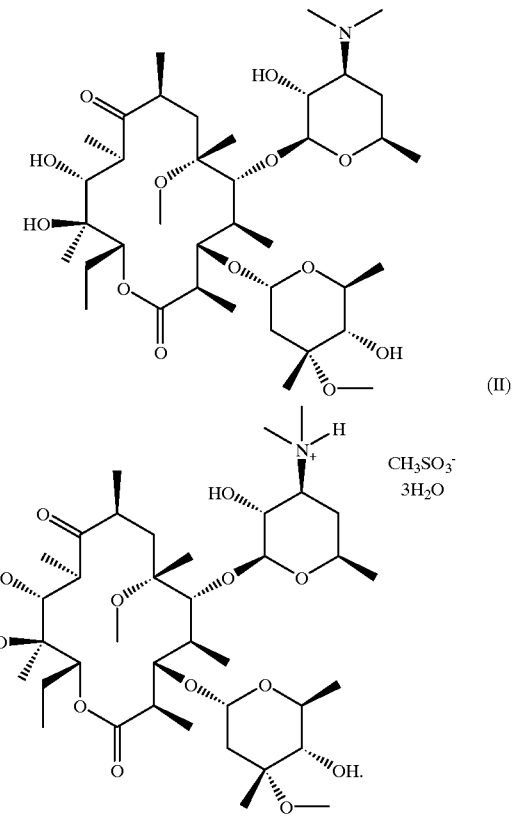

2. The method of claim 1, wherein the non-pharmaceutical grade clarithromycin used in step (a) is prepared by a process comprising the steps of:

protecting the 9-oxime hydroxy group of erythromycin A 9-oxime of formula (IV) or a salt thereof with a tropyl group and the 2'- and 4"-hydroxy groups with trimethylsilyl groups to obtain 2',4"-O-bis(trimethylsilyl) erythromycin A 9-O-tropyloxime of formula (IIIb);

reacting 2',4"-O-bis(trimethylsilyl)erythromycin A 9-O-tropyloxime with a methylating agent to obtain 2',4"-O-bis(trimethylsilyl)-6-O-methylerythromycin A 9-O-tropyloxime of formula (IIIc); and removing the protecting groups and the oxime group of 2',4"-O-bis(trimethylsilyl)-6-O-methylerythromycin A 9-O-tropyloxime:

(IV)

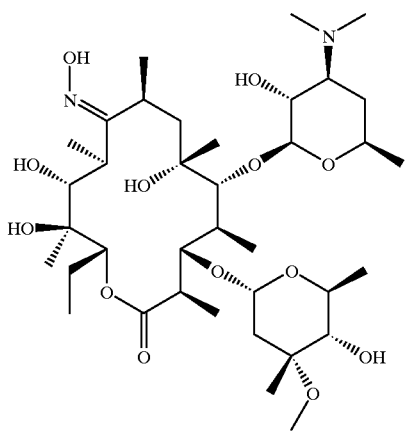

(IIIb)

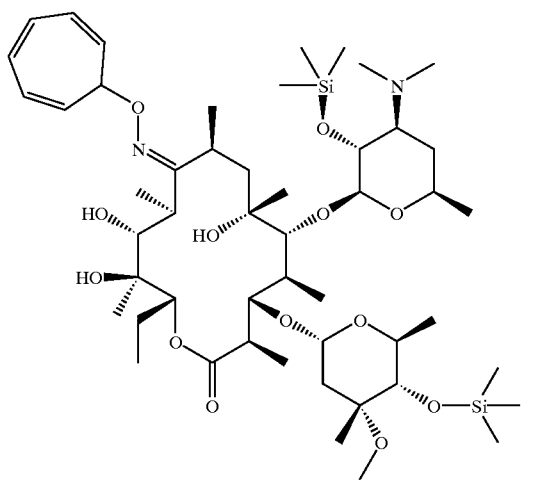

(IIIc)

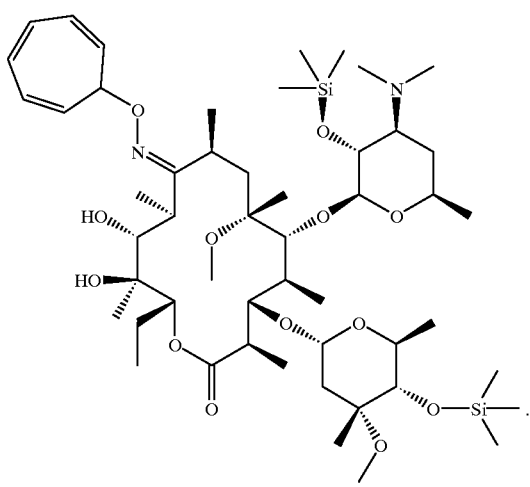

3. The method of claim 2, wherein 2',4"-O-bis(trimethylsilyl)erythromycin A 9-O-tropyloxime of formula (IIIb) is prepared in accordance with a process comprising the steps of:

reacting erythromycin A 9-oxime with tropylium tetrafluoroborate in an aprotic polar solvent in the presence of a base at a temperature ranging from 0 to 60° C. to obtain erythromycin A 9-O-tropyloxime; and treating erythromycin A 9-O-tropyloxime with ammonium chloride and 1,1,1,3,3,3,-hexamethyldisilazane in an organic solvent at a temperature ranging from room temperature to 50° C.

4. The method of claim 2, wherein 2',4"-O-bis(trimethylsilyl)erythromycin A 9-O-tropyloxime of formula (IIIb) is prepared in accordance with a process comprising the steps of:

reacting erythromycin A 9-oxime or a salt thereof with ammonium chloride and 1,1,1,3,3,3- hexamethyldisilazane in an organic solvent at a temperature ranging from room temperature to 50° C. to obtain 2',4"-O-bis(trimethylsilyl)erythromycin A 9-oxime; and reacting 2',4"-O-bis(trimethylsilyl)erythromycin A 9-oxime with tropylium tetrafluoroborate in an aprotic polar solvent in the presence of a base at a temperature ranging from 0 to 60° C.

5. The method of claim 3, wherein the aprotic polar solvent is tetrahydrofuran, 1,4-dioxane, ethyl acetate, acetonitrile, N,N-dimethylformamide, dichloromethane or a mixture thereof.

6. The method of claim 3, wherein the base is triethylamine, tripropylamine, diethylisopropylamine, tributylamine, 1,8-diazabicyclo[5.4.0]undec-7-ene, 1,5-diazabicyclo[4.3.0]non-5-ene, 1,4-diazabicyclo[2,2,2]octane, sodium carbonate, potassium carbonate, sodium hydroxide, potassium hydroxide, potassium t-butoxide, sodium hydride or a mixture thereof.

7. The method of claim 2, wherein 2',4"-O-bis(trimethylsilyl)-6-O-methylerythromycin A 9-O-tropyloxime of formula (IIIc) is prepared by reacting 2',4"-O-bis(trimethylsilyl)erythromycin A 9-O-tropyloxime with methyl iodide in an organic solvent in the presence of a base at a temperature ranging from 0 to 10° C.

8. The method of claim 7, wherein the organic solvent is a mixture of tetrahydrofuran and dimethyl sulfoxide; and the base is potassium hydroxide, potassium hydride, potassium t-butoxide, sodium hydride, or a mixture thereof.

9. The method of claim 2, wherein the step of removing the protecting groups and the oxime group of 2',4"-O-bis(trimethylsilyl)-6-O-methylerythromycin A 9-O-tropyloxime is carried out by treating it with formic acid and sodium bisulfite in an alcoholic aqueous solution at a temperature ranging from room temperature to the boiling point of the solvent.

10. The method of claim 1, wherein the mixture used in step (a) contains water in an amount ranging from 3 to 15 equivalents based on the amount of clarithromycin.

11. The method of claim 1, wherein the water-miscible organic solvent is acetone, ethanol, isopropanol, or a mixture thereof.

12. The method of claim 1, wherein methanesulfonic acid is used in amount ranging from 0.9 to 1.1 equivalents based on the amount of clarithromycin.

13. The method of claim 1, wherein the mixture used in step (b) is composed of a water-miscible organic solvent and water in a volume ratio of 30:70 to 70:30.

14. The method of claim 1, wherein the neutralization step (b) is conducted to a pH in the range of 9 to 12.

15. Clarithromycin mesylate trihydrate of formula (II):

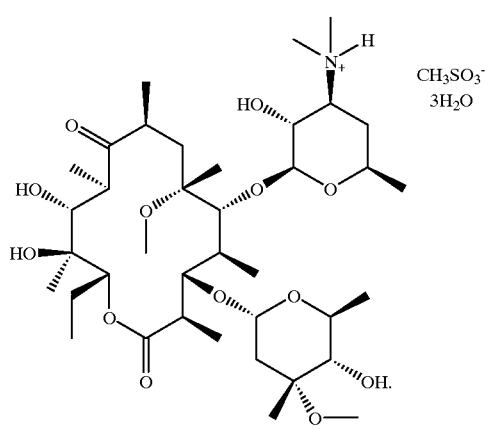

(II)

16. Erythromycin A 9-O-tropyloxime derivative of formula (III);

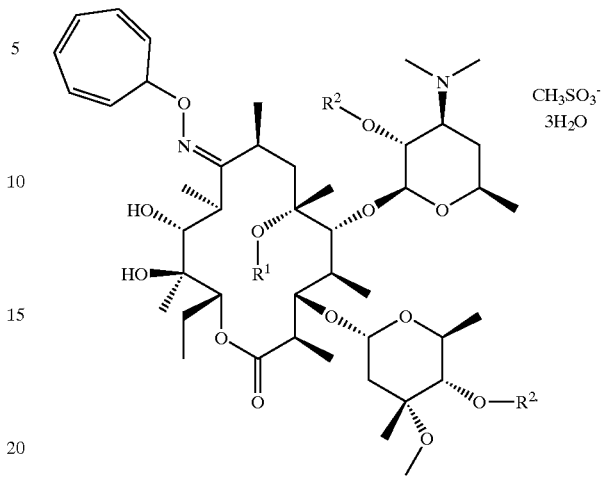

(III)

wherein,
R$^1$ is hydrogen or methyl; and
R$^2$ is hydrogen or trimethylsilyl (if R$^1$ is methyl, R$^2$ is trimethylsilyl).

17. The method of claim 4, wherein the aprotic polar solvent is tetrahydrofuran, 1,4-dioxane, ethyl acetate, acetontrile, N,N-dimethylformamide, dichloromethane or a mixture thereof.

18. The method of claim 4, wherein the base is triethylamine, tripropylamine, diethylisopropylamine, tributylamine, 1,8-diazabicyclo[5.4.0]undec-7-ene, 1,5-diazabicyclo[4.3.0]non-5-ene, 1,4-diazabicyclo[2.2.2]octane, sodium carbonate, potassium carbonate, sodium hydroxide, potassium hydroxide, potassium t-butoxide, sodium hydride, or a mixture thereof.

* * * * *